(12) United States Patent
Esposito (10) Patent No.: US 11,494,901 B2
(45) Date of Patent: Nov. 8, 2022

(54) DIGITAL TELEPATHOLOGY AND VIRTUAL CONTROL OF A MICROSCOPE USING EDGE COMPUTING

(71) Applicant: Saint Louis University, St. Louis, MO (US)

(72) Inventor: Flavio Esposito, St. Louis, MO (US)

(73) Assignee: Saint Louis University, St. Louis, MO (US)

(*) Notice: Subject to any disclaimer, the term of this patent is extended or adjusted under 35 U.S.C. 154(b) by 350 days.

(21) Appl. No.: 16/880,489

(22) Filed: May 21, 2020

(65) Prior Publication Data

US 2020/0372643 A1 Nov. 26, 2020

Related U.S. Application Data

(60) Provisional application No. 62/850,744, filed on May 21, 2019.

(51) Int. Cl.
| | |
|---|---|
| *G06K 9/00* | (2022.01) |
| *G21K 7/00* | (2006.01) |
| *G06T 7/00* | (2017.01) |
| *G16H 30/20* | (2018.01) |
| *G02B 21/36* | (2006.01) |

(52) U.S. Cl.
CPC .......... *G06T 7/0012* (2013.01); *G02B 21/365* (2013.01); *G06T 7/97* (2017.01); *G16H 30/20* (2018.01); *G06T 2207/10016* (2013.01); *G06T 2207/30096* (2013.01)

(58) Field of Classification Search
CPC .................. G06K 9/00; G21K 7/00
USPC ....... 382/100, 103, 106, 128–134, 156, 162, 382/168, 173, 181, 199, 209, 219, 224, 382/232, 254, 274, 276, 291, 305, 321; 375/E7.263; 378/43
See application file for complete search history.

(56) References Cited

U.S. PATENT DOCUMENTS

| | | | | |
|---|---|---|---|---|
| 5,297,034 A | * | 3/1994 | Weinstein | H04N 7/183 382/128 |
| 5,432,871 A | * | 7/1995 | Novik | H04N 19/503 375/E7.263 |
| 6,674,884 B2 | * | 1/2004 | Bacus | G06T 7/0012 382/133 |
| 7,916,916 B2 | | 3/2011 | Zeinch | |
| 2009/0169090 A1 | * | 7/2009 | Griffin | G06T 7/12 382/133 |
| 2016/0062101 A1 | | 3/2016 | Weiss et al. | |

(Continued)

FOREIGN PATENT DOCUMENTS

| | | |
|---|---|---|
| CN | 105357304 B | 2/2016 |
| CN | 106446568 A | 2/2017 |

(Continued)

*Primary Examiner* — Seyed H Azarian
(74) *Attorney, Agent, or Firm* — Polsinelli PC (57) ABSTRACT

A telepathology system is associated with an edge network shared among participating users for remote control of a microscope. The microscope includes a camera operable to receive image data of a specimen. The telepathology system is capable of receiving image data from the microscope, pre-processing the image data at network edge, sending the pre-processed image digitally to the participating users via a web server on the edge network, and controlling the image data, via instructions from the participating users.

12 Claims, 8 Drawing Sheets

(56) References Cited

U.S. PATENT DOCUMENTS

2017/0299496 A1* 10/2017 Balagurusamy ........ G06T 7/246
2022/0058708 A1*  2/2022 Papp ...................... G16B 50/30

FOREIGN PATENT DOCUMENTS

| JP | 3698737 B2 | 9/1994 |
| WO | 199903026 A1 | 1/1999 |
| WO | 1999013360 | 3/1999 |
| WO | 2009095926 A1 | 8/2009 |
| WO | 2013142219 A1 | 9/2013 |

* cited by examiner

DIGITAL TELEPATHOLOGY AND VIRTUAL CONTROL OF A MICROSCOPE USING EDGE COMPUTING

CROSS-REFERENCE TO RELATED APPLICATIONS

This application claims the benefit under 35 U.S.C. § 119(e) of U.S. Provisional Application No. 62/850,744, filed May 21, 2019, the entire contents of which are incorporated herein by reference in their entirety.

FIELD

The present disclosure relates generally to systems and methods for digital telepathology and virtual control of a microscope via edge computing for image and network processing. In at least one example, the present disclosure relates to systems and methods to allow remote users to control the microscope simultaneously with responsiveness, to process microscopy imagery and live video, and to enforce secure transfers and preserve privacy creating virtual private shared data views.

BACKGROUND

Pathologists diagnose histological images with a physical multi-lens microscope, manually moving glass slides, adjusting focus and switching lens to explore the area of interest. A pathologist may analyze histological images on a glass slide while the patient is still under a tumor removal surgery. Hence, a quick pathology assessment is crucial for the patient. In the vast majority of non-trivial pathology cases, to minimize the time for response to the surgeon team and the probability of incorrect assessments, pathologists ask for second opinions to nearby experts (if available) by physically carrying privacy-protected glass specimens. Hospitals in rural areas are often forced to outsource pathology cases, incurring significant costs and delays.

In theory, current telepathology solutions are limited by the technology, the (best-effort) performance of the underlying telecommunication media on which they rely on, i.e., the Internet, and by its end-to-end bandwidth optimizations. In practice, telepathology solutions at best use a virtual private network for in-hospital offline, i.e., non-real-time, consultations.

Therefore, there is a need for a telepathology system and methods of use to allow real-time remote control of a microscope and real-time histological image processing.

SUMMARY

In an aspect, a telepathology system associated with an edge network shared among participating users includes a microscope comprising a camera operable to receive image data of a specimen; one or more processors connected to the edge network; and a memory storing instructions that, when executed by the one or more processors, cause the one or more processors to: receive image data from the camera; pre-process the image data at network edge; send the pre-processed image data digitally to the participating users and receive control instructions from the user, wherein the control instructions, when executed by the one or more processors, cause the one or more processors to control the image data. In at least one aspect, the image data is histological image data.

In some aspects, the memory stores further instructions to speed up image transmission time and/or perform application-specific image processing. In some aspects, the memory stores further instructions to assign a dedicated Virtual Node instance, for example a Virtual Machine (VM) or a Lightweight Virtual Machine to each participating user. In some aspects, the control of the image data is selected from moving the microscope platform, panning, zooming, and/or capturing at least one additional image for live or subsequent processing.

In some aspects, the image data is a still image or a video. In at least one aspect, the image data is video and the memory stores further instructions to live stream the specimen to the participating users. In at least one aspect, the edge network pre-processes the stream, compressing its payload.

In some aspects, the memory stores further instructions to process the image data to identify a property of the specimen. In at least one aspect, the property of the specimen is selected from color decomposition, cell count, count of nuclei of proliferating tumor cells, distinction of non-tumor vs. tumor, and/or percentage of cells activated by different markers.

In an aspect, a telepathology method includes receiving image data from a microscope (real or emulated via software comprising a camera operable to receive image data of a specimen, wherein the microscope is associated with an edge network shared among participating users; pre-processing the image data at network edge; sending the pre-processed image digitally to the participating users; and controlling the image data, via instructions from the participating users. In at least one aspect, the image data is histological image data.

In some aspects, the method further includes speeding up image transmission time and/or performing application-specific image processing. In some aspects, the method further includes assigning a dedicated physical or virtual node instance (for example a VM or a Lightweight VM) to each participating user. In some aspects, controlling of the image data is selected from panning, zooming, and/or capturing at least one additional image for live or subsequent processing.

In some aspects, the image data is a still image or a video. In at least one aspect, the image data is video and sending the image data comprises live streaming the specimen to the participating users.

In some aspects, the method further includes processing the image data to identify a property of the specimen. In at least one aspect, the property of the specimen is selected from color decomposition, cell count, count of nuclei of proliferating tumor cells, distinction of non-tumor vs. tumor with a static image, distinction of non-tumor vs. tumor as the participating user moves the image, and/or percentage of cells activated by different markers.

BRIEF DESCRIPTION OF THE DRAWINGS

Implementations of the present technology will now be described, by way of example only, with reference to the attached figures, wherein.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The terms "comprising," "including" and "having" are used interchangeably in this disclosure. The terms "comprising," "including" and "having" mean to include, but not necessarily be limited to the things so described.

The term "telepathology" is the practice of digitizing histological images for transmission along telecommunication pathways for diagnosis, consultation or continuing medical education.

Existing telepathology solutions do not use edge computing, so they are limited to non-interactive and unprocessed image transfers and often rely on standard Internet connections. On the Internet, traffic flows compete, reducing speed and increasing delays. Existing telepathology systems are based on time-consuming digital compositions and transmission of large images captured from cameras attached to the microscope. Advanced layer2 network functionally, for example those used to build the GENI or FABRIC testbed, and using for example Internet2, and ESnet can similarly extend high-performance paths across the regional, national, and international network transit providers. Solutions have attempted to connect a microscope over virtual paths with guaranteed performance. Other studies designed expensive arrays of microscope processors to capture images, as well as inexpensive solutions using images captured using smartphones or cameras on board of a Raspberry Pi for telecytology. In the latter solution, images were transferred using FaceTime (hence in a broadcast, without the ability to remotely control the microscope).

Telepathology today is practically unused for the applications that would need it the most: delay and bandwidth sensitive data processing and sharing, fast and reliable remote consultations, and multi-user live educational sessions.

Provided herein is an edge computing-based telepathology system that allows real-time remote control of the microscope and real-time histological image processing. In particular, the system and methods thereof may have capabilities of rapid processing of histological images, and with low-latency image transmissions. The telepathology system provided herein may have improved speed and accuracy of pathology assessments by enabling remote computation and remote consultation. When not enough local experts are available, the presence of a telepathology system may be a critical factor in providing the best care for the patient. Moreover, a telepathology system can be used to transmit high resolution images of specimens to connected experts in order to speed up the diagnosis of more routine cases in more rural treatment locations. A telepathology system may also mitigate discordance between pathologists. Pathologists will substantially benefit from remotely browsing, zooming and panning massive images at exceptionally high-speeds and resolution—similar to what they use when handling the microscope glass locally. Examples of edge computing tasks include payload optimization methods such as compression algorithms and high resolution image format conversion, and pattern matching algorithms to identify biological markers of tumors on the image under investigation and suggest automatically the tumor grade.

The telepathology system enables remote collaboration and digital image sharing in addition to remote computation provided by edge computing. For example, the telepathology system allows a team of pathologists to access, control and process, simultaneously, a remotely located (real or emulated) microscope using merely a (mobile) web browser. The telepathology system may improve the field of medical diagnosis in critical situations, for example under an active surgery, where a quick diagnosis is literally vital but experts are locally unavailable. In addition, the telepathology system may eliminate the need to transfer physical slides and remove the travel time for remote specialists for consults or tumor board reviews. As demonstrated, this saves valuable time and expense, providing faster diagnoses resulting in better patient care.

The edge computing-empowered microscope may provide additional benefits such as speeding up image and video transmission time and performing application-specific image processing. Such processing may include tumoral cell identification to speed up pathology diagnosis (currently expressed cells are manually counted) and to support pathologies in continuous education.

In an example, the telepathology system may be used to connect experts with patient data, allowing transmission of high-resolution images of specimens. This allows rapid diagnosis of complex cases even in geographical areas that lack local expertise. In some examples, the telepathology system may be affordable, high-throughput, support low latency access to a remotely controlled microscope, and have the ability to process imagery at the edge of the network before or after their transfer. Often, an experienced or expert pathologist may not be at the hospital, or even in the same city, when an assessment or diagnosis is needed in a short amount of time to inform surgery or treatment protocol. In various examples, the telepathology system may provide real-time, remote consultations for unspecialized pathologists on difficult cases, real-time consultations on rare or newly recognized diseases, a reduction in the risk of malpractice, remote routine assessments for consolidation of resources, and/or remote computation to speed up both human and machine learning training for research discoveries and future clinical diagnostics.

The telepathology system may significantly advance the field of telepathology by augmenting live remote microscope sessions with the computational power of edge computing technologies. Such a platform allows a team of pathologists to access, control, and process, simultaneously, a remotely located (real or emulated) microscope using merely a (mobile) web browser. The architecture of the telepathology system has the potential to improve the field of medical diagnosis in critical situations, for example under an active surgery, where a quick diagnosis is vital but experts are locally unavailable.

Furthermore, an edge computing-empowered microscope provides additional benefits such as performing application-specific image processing and speeding up image transmission time. Such processing involves, for example, tumoral cell identification to accelerate pathology diagnosis and to support pathologies in continuous education.

Figure 9:
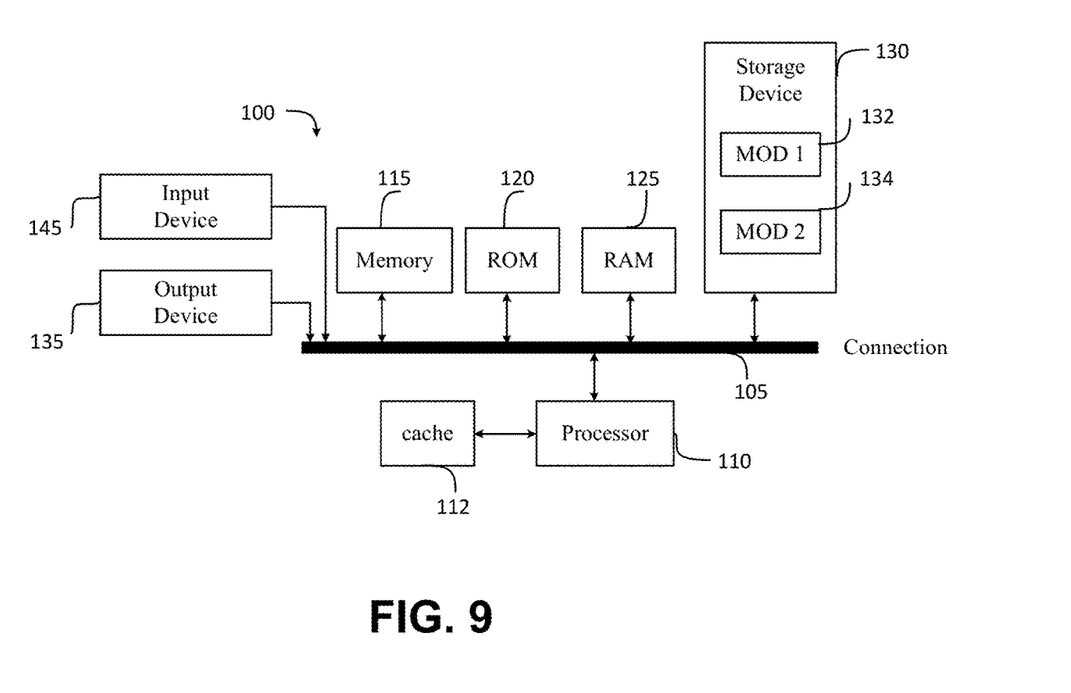
FIG. 9 shows a computing system for a telepathology system in one example.

FIG. 9 shows an example of computing system 100 in which the components of the system are in communication with each other using connection 105. Connection 105 can be a physical connection via a bus, or a direct connection into processor 110, such as in a chipset or system-on-chip architecture. Connection 105 can also be a virtual connection, networked connection, or logical connection.

In some examples, one or more of the described system components represents many such components, each performing some or all of the functions for which the component is described. In some examples, the components can be physical or virtual devices.

Example computing system 100 includes at least one processing unit (CPU or processor) 110 and connection 105 that couples various system components including system memory 115, read only memory (ROM) 120, or random access memory (RAM) 125 to processor 110. Computing system 100 can include a cache of high-speed memory 112 connected directly with, in close proximity to, or integrated as part of processor 110.

Processor 110 can include any general-purpose processor and a hardware service or software service, such as an acquisition system 132 and data processing system 134 stored in storage device 130, configured to control processor 110 as well as a special-purpose processor where software instructions are incorporated into the actual processor design. Processor 110 may essentially be a completely self-contained computing system, containing multiple cores or processors, a bus, memory controller, cache, etc. A multi-core processor may be symmetric or asymmetric.

To enable user interaction, computing system 100 includes an input device 145, which can represent any number of input mechanisms, such as a touch-sensitive screen for gesture or graphical input, keyboard, mouse, or input from the participating users. The input device 145 may be wired or wireless. Computing system 100 can also include output device 135, which can be one or more of a number of output mechanisms known to those of skill in the art. For example, the output device 135 may be a display or may be transmitted to participating users. In some instances, multimodal systems can enable a user to provide multiple types of input/output to communicate with computing system 100. There is no restriction on operating on any particular hardware arrangement, and therefore the basic features here may easily be substituted for improved hardware or firmware arrangements as they are developed.

Storage device 130 can be a non-volatile memory device and can be a hard disk or other type of computer readable media which can store data that is accessible by a computer, such as magnetic cassettes, flash memory cards, solid state memory devices, digital versatile disks, cartridges, battery backed random access memories (RAMs), read only memory (ROM), and/or some combination of these devices.

The telepathology system may include a microscope and a computing system connected to the microscope that includes software services, servers, services, etc. that, when the code that defines such software is executed by the processor 110, it causes the system to perform a function. In some examples, a hardware service that performs a particular function can include the software component stored in a computer-readable medium in connection with the necessary hardware components, such as processor 110, connection 105, output device 135, etc., to carry out the function. In some examples, the storage device 130 includes an acquisition system 132 and a data processing system 134. The acquisition system 132 may include instructions to cause the processor 110 to control the microscope, support network connectivity or edge computing functionalities. The data processing system 134 may include instructions to cause the processor 110 to speed up image and video transmission time and/or perform application-specific image processing.

The telepathology system may enable pathologists to remotely visualize histological images on a remotely-controllable microscope emulator. The web based front-end allows pathologists located in remote locations to sign up, login, join a session and interact with a microscope. Interaction may include, but is not limited to pan, zoom, or capture images for live or subsequent processing. Commands may be sent via a protocol so that feedback on the remote microscope action is immediate, when enough network bandwidth is available. The back-end of the system may include an edge cloud. In at least one example, the edge cloud may be based on an enhanced version of a cloud or edge cloud orchestrator, for example, OpenStack. Images or videos captured by the microscope may be pre-processed at network edge and then may be sent, digitally, to the pathologist client via a web server. In an example, the system may integrate the edge network into OpenStack to provide an adequate scheduling of resources.

The telepathology system may allow remote control of human pathology gestures on a microscope, via "software-defined glass slides". In the disclosed telepathology system, the resolution, responsiveness, and size of the histological images to transfer and preprocess can be large, but very low delays and high throughput are required. None of these requirements were simultaneously tackled in previous solutions. In an example, detection requests for pattern or objects have been processed in proximity of the source of information.

The telepathology system may allow for prescreened, "augmented" histological images for real-time, intraoperative and second opinion specialist consultations. Augmented histological images may be processed at the edge of the network, i.e., physically close to the microscope. For example, identification of a few abnormal cells among thousands of normal cells in a cervical Pap smear saves diagnosticians time, by bypassing the need to screen an entire slide, allowing focus on the relevant, abnormal cells. It may provide dedicated cyberinfrastructures that may isolate and monitor network traffic moving between distributed edge systems and campus resources to large-scale centralized compute and storage resources, e.g., large computing centers, public and private clouds, and remote data repositories. These advancements in federated cyberinfrastructure will enable sessions in which telepathology can be effectively performed across geographically distributed sites.

The telepathology system may be used in any field that uses a microscope, for example, pathology, histology, or microbiology.

Figure 10:
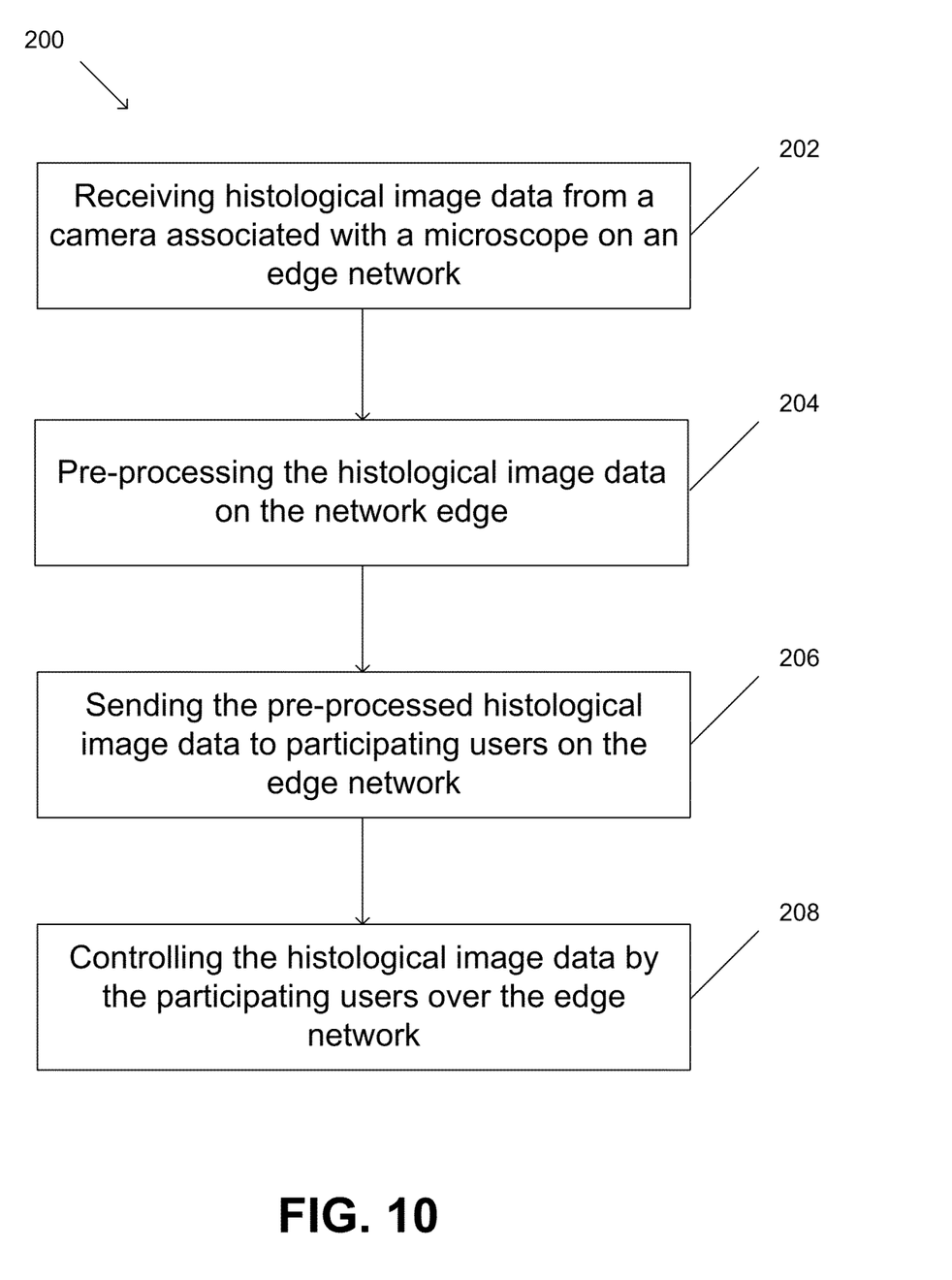
FIG. 10 shows a method of using a telepathology system in one example.

Referring to FIG. 10, a flowchart is presented in accordance with an example aspect. The method 200 is provided by way of example, as there are a variety of ways to carry out the method. The method 200 described below can be carried out using the configurations illustrated in FIG. 1, 3, 4, or 11, for example, and various elements of these figures are referenced in explaining example method 200. Each block shown in FIG. 10 represents one or more processes, methods or subroutines, carried out in the example method 200. Furthermore, the illustrated order of blocks is illustrative only and the order of the blocks can change according to the present disclosure. Additional blocks may be added or fewer blocks may be utilized, without departing from this disclosure.

The example method 200 is a method of remotely controlling a microscope by participating users on an edge network. In at least one example, the microscope may be part of a telepathology system. Accordingly, with the method 200, the participating user(s) does not have to be located physically near the microscope. The example method 200 can begin at block 202.

At block 202, image data is received from a camera associated with a microscope connected to an edge network. In at least one example, the image data can be a still image or video. In at least one example, the image data is histological image data.

At block 204, the image data is pre-processed at the network edge.

At block 206, the pre-processed image data is sent to participating users on the edge network. In an example, the image data is a still image. In another example, the image data is video that is compressed and live streamed to the participating users. In at least one example, the image data is histological image data.

At block 208, the microscope may be controlled by the participating users over the edge network, in response to the pre-processed image data received by the users. In some examples, control of the microscope is selected from moving the microscope platform, panning, zooming, and/or capturing at least one additional image for live or subsequent processing. In an example, control of the microscope may include control of the image data. In at least one example, the image data is histological image data.

EXAMPLES

Example 1: Architecture and Processing

The telepathology system may allow remote computations and remote consultations. Remote consultation means the possibility for pathologists to request remote access through a front-end interface to a live session of a microscope and remotely control its software, firmware and its functionalities. Typically, pathologists ask for panning, zooming or taking snapshots of histological samples. To manage each telepathology session, the back-end edge cloud system assigns a dedicated (Lightweight) Virtual Machine to each user.

Example 2: Front-End and Plugin Design

Figure 1:
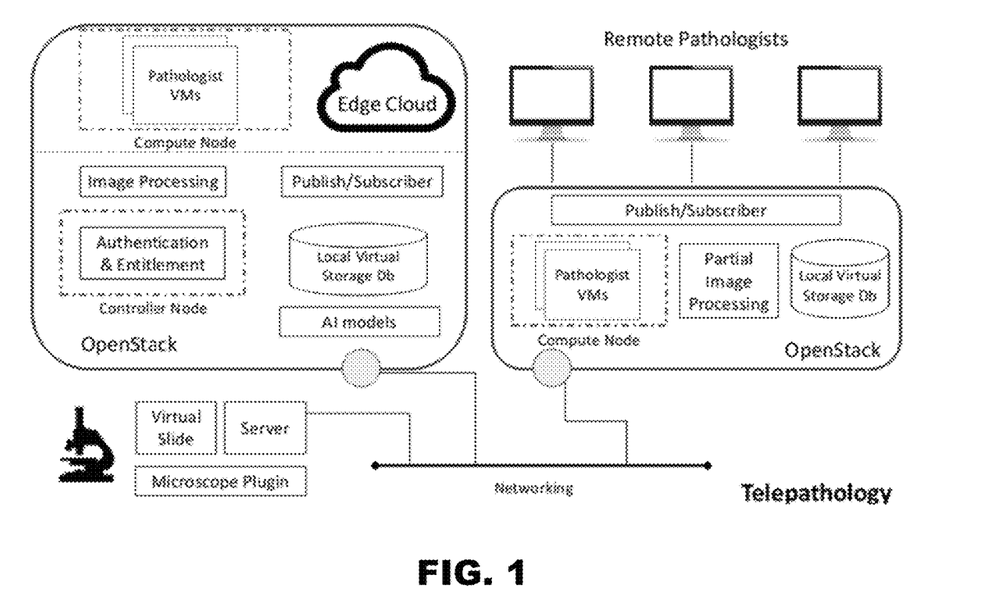
FIG. 1 shows the telepathology subsystem and services.
Figure 2:
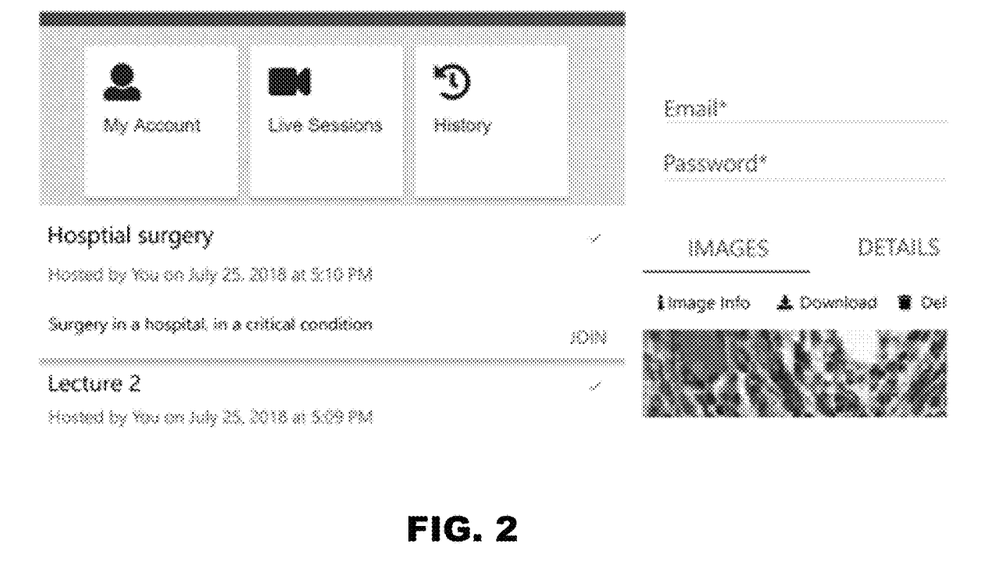
FIG. 2 shows screenshots of the web interface of the application. From the top left to the bottom left: home page, login page, real-time view of histological images, list of live sessions currently active.

The telepathology system allows pathologists to be able to access the microscope in a user-friendly manner, by merely using a mobile web browser. The web server is the entry point for the entire system and acts as a portal through which users connect to the telepathology system and start, join, or terminate one or multiple telepathology sessions. In an example, the telepathology system is lightweight, with an intuitive and user-friendly design. In an example, the web interface (FIG. 2) may be implemented in AngularJS and the slide visualization may be managed by the OpenSeadragon JavaScript library.

In at least one example, the processing system runs a modified version of μManager—often named Micro-Manager, as in microscope-manager—an open-source package for controlling and configuring a fairly large amount of commonly used microscopes. μManager did not support network connectivity or edge-computing functionalities. The modified instance of μManager can be plugged into a physical machine attached to a microscope, to handle data marshaling between the network and the microscope firmware. It can also be attached to a microscope emulator. In an example, the telepathology system may use a microscope whose interface is compatible with Micro-Manager (i.e., Olympus IX81). The telepathology system also supports an emulated version of the microscope, which may be an effective tool to scale, for example for pathology medical education, for distributed machine learning training, and to avoid binding to a specific hardware camera.

Since pathologists (in training or at work) need to switch microscope lenses and examine tissues looking for patterns, a simple image snapshot is often not enough. Live streaming of the sample under consideration hence provides an immediate feedback and makes the system usable. In an example, ffmpeg may be used to encode and transmit videos between a Micro-Manager Plugin (from now on denoted as, Plugin) and the telepathology system server, while on the web-page, the WebRTC plugin may be responsible for receiving and showing the video. The edge cloud pre-processes the stream, compressing its payload. The compression is not performed on the Plugin, but in a second phase, thereby videos can be stored for pre-processing or retrieved at a later stage.

Example 3: Core and Edge Cloud Management

To control large pools of computing, storage, and networking resources between the web server and the μManager plugin, an Edge Cloud infrastructure was deployed (FIG. 1), modifying the OpenStack open-source Cloud Computing platform. Each user of a telepathology session may be associated to a (lightweight) Virtual Machine (VM); if needed, each virtual instance can provide network or node functionalities, e.g., CPU-intensive algorithms on the histological imagery.

In an Edge Computing system, much of the processing takes place in a process at the edge of the network (as opposed to the core of the network as in the Cloud Computing paradigm). It is inefficient to transmit all telepathology generated data to the cloud for processing, data query or analysis; doing so consumes a great deal of bandwidth and all the back-and-forth communications between the sensors and the cloud would adversely impact performance, rending the application unusable. The present edge computing infrastructure may enable flexibility in the mechanisms that regulate the adaptation (creation, monitoring, and migration) of virtual network resources carrying glass-slide imagery.

The edge computing architecture may use at least two nodes (hosts) responsible for launching the core management functionalities: the controller node and the compute node. The controller manages the resources available in the infrastructure, and the compute node runs the VMs and their bookkeeping; the networking service agent then connects all telepathology instances to their isolated virtual networks, providing firewalling services to instances via security groups.

The choice of the best hosting machine is based on some configurable criteria, e.g., hosted application requirements or the usage of machines at that moment. By default, the edge cloud manager software selects the hosting machine independently from the application logic. In the present system, the controller node was forced to choose a node near the requested microscope, to guarantee low delay. Specifically, the default cloud orchestration mechanisms were adjusted to better support edge computing applications, modifying the VM scheduler to handle multiple telepathology sessions.

Example 4: Telepathology System Server

Figure 3:
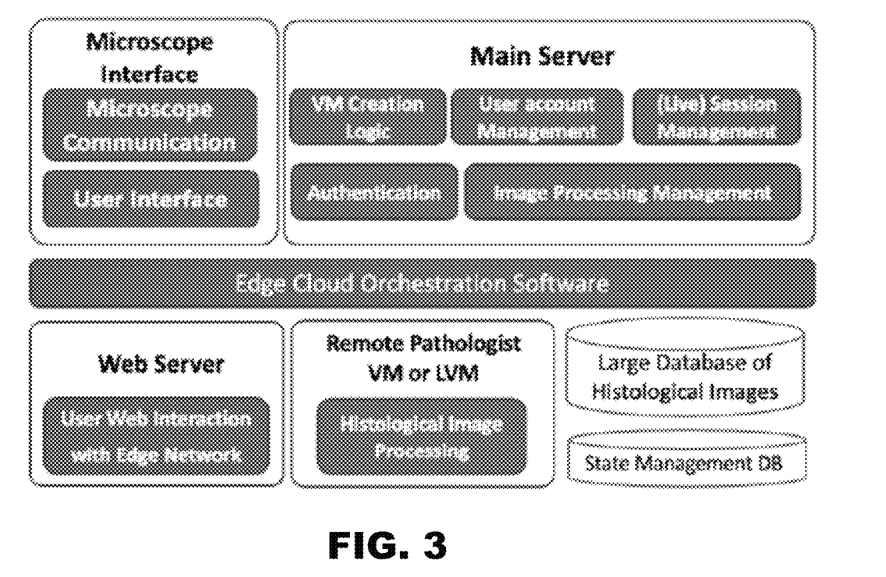
FIG. 3 shows the overall telepathology system architecture, where the boxes are the telepathology system's implemented services.

FIG. 3 shows the architecture of the telepathology system, highlighting the key mechanisms provided by each component. The Main Server of the telepathology system is the core process that runs most of the logic of the application. It can receive requests from the web server or from the microscope (emulator) plugin, and it is responsible for the following tasks: it manages live sessions, it communicates with the database and decides when it is time to create or destroy a VM, according to the business logic. In the telepathology system, to reduce the startup delay when a VM is created, a pool of VMs are kept already deployed. In such a way, when a user needs to operate on a VM, the system can exploit the existing VMs instead of creating new ones, hence reducing the response time.

The Main Server also provides the services for remotely controlling the microscope. In addition, this server is responsible for the management of the prior (live) sessions and to handle the API calls launched by the emulator plugin and the desktop application, for example using the Node.js REST API.

A telepathology session client runs on each VM and acts as a proxy: it receives requests from the Main Server through, for example, using the Node.js REST API gRPC protocol, elaborates them and in case sends them to plugin. The requests are not forwarded if the response is already in process on the VM, e.g., the client is working on an already-snapped image. This cache layer avoids overloading the real microscope.

The image and video processing of each telepathology session can span across multiple VMs. Hence, each client can ask for different processing, at the same time, on the same virtualized histological image. The system assures that actions of a user do not affect the analysis of another pathologist working on the same sample, because the operations take place in different VMs. The pathologist is free to work independently as long as the action does not modify the microscope settings. In this latter case, the actions are enqueued and synchronized, and all the clients of the sessions will be affected. This strategy is based on the intuition that users are more likely to require image and video processing rather than microscope configuration. The synchronization prevents the access to the shared resource (the microscope) from multiple agents that can potentially lead to an inconsistent state. However, the time to execute actions is significantly smaller than transmission and processing time, proving that, when ten users are cooperating, the waiting time is negligible.

Example 5: Image Management and Visualization

The pathologist can analyze images that are captured in real-time or that were previously saved. In the former case, there is not enough time to generate a WSI and, for this reason, the system sends only the slide as captured by the camera. If requested, the image is processed, but the algorithm is limited to the viewed image only.

In the latter case, i.e., offline digital slides, the web application may use the OpenSeadragon image viewer for navigating and zooming over the slide. On the server side, specifically on the VM, the telepathology program returns tiles of specified coordinates and zoom levels on demand. These images are large and require enough disk space to store them, thus the RAM usage is optimized by loading not the entire image, but only a small portion of it, i.e., a tile. These tiles are generated on demand using a software tool that generates, for example, the open source Pyramidlo. Pyramidlo allows reading WSIs of different formats and facilitates the rapid retrieval of subregions of the image. The tiles could also be pre-generated and saved on the file system for future usage. Nonetheless, performance differences between dynamically tiled and statically tiled viewing sessions were imperceptible for the user. Moreover, the use of dynamic tiling avoids an additional step in the workflow and eliminates the storage overhead of storing tiles.

Alongside the management of smaller tiles, the VM provides a cache layer between the client and the storage, so that multiple requests for the same area are immediately replied. In such a way, the time to process a request is shortened. Additionally, the web browser, through the OpenSeadragon library, is a supplemental layer for caching the image bytes, in order to reduce the response time.

Example 6: Live Streaming Architecture for Immediate Medical Feedback

Immediate feedback obtained from the system and live streaming from the microscope camera is an effective way to give this feedback to the medical doctor. In the telepathology system, the remote pathologist can manipulate the microscope in search of the best possible sample for the diagnosis.

In order to provide the video streaming to all the pathologists connected to the live session, ffmpeg is leveraged as an encoder, and WebRTC as a de-multiplexer and for showing the video in the web-page.

At the plugin side, the frame encoding occurs via a software, for example ffmpeg, which reads from files the frames captured by the subsystem connected to the microscope, e.g., Micro-Manager, and sends such frames as a stream to the Main Server. This tool allows specifying significant video options, such as aspect ratio, video codec, frame rate. These parameters are set to guarantee low delays and to achieve zero losses in the capture, therefore moderately sacrificing the video resolution. Nonetheless, as in the edge computing paradigm, the Main Server is in the proximity of the Plugin, which allows not to drastically downgrade the video resolution in favor of the latency. Besides, the stream is directly sent to the Main Server rather than passing through the user's VM, in order to further reduce the application delay. It is also worth noticing that very high-resolution images, when needed, can be obtained by means of offline downloads.

On the Server resides a transmission manager, for example, WebRTC, which manages the imagery stream to the final user. This transmission manager is responsible for communicating with the web browser in order to agree on an appropriate bitrate that adapts to the network conditions. This service receives the stream of data from the microscope firmware (e.g., the Micro-Manager Plugin) and forwards it to clients interested in receiving the video. In case the client asks for a reduced bitrate compared to the ffmpeg stream, the transmission manager handles this difference and stores the data temporarily in order to synchronize the incoming stream with the outgoing one. Moreover, the transmission manager receives the commands from the user and forwards them to the microscope, dispatching the requests in the same or a different (i.e,. priority-based) order in which they are received, depending on the configuration policy.

The transmission manager comes up with several components for different functionalities provided. Among them, signal processing, codec handling, security, and bandwidth management may be enumerated.

Figure 4:
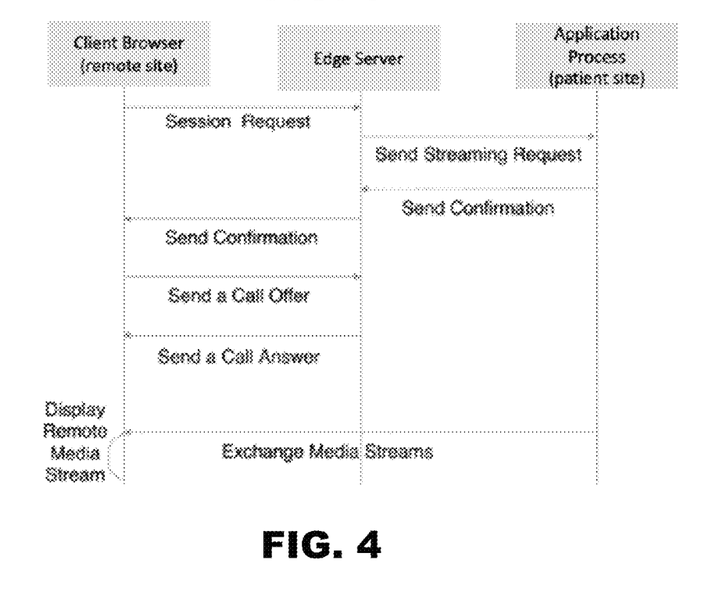
FIG. 4 shows example signaling and interaction of video streaming.

FIG. 4 summarizes the messages defined to instantiate the streaming from the microscope to the connected user, as well as signaling requirements and interactions. The transmission manager is responsible for managing the full life cycle of each client-microscope connection at the remote site, by encapsulating all the connection setup, management, and state within a single interface. When the user joins a live session, it contacts the signal server to create the session and a secure channel. Once the server receives the request, it starts the streaming session. At this point, the Plugin initializes the samples capture procedure and sends the confirmation back, which is eventually forwarded from the Server to the client. Then, the client sends an offer message containing a description of the streaming session, for example, according to a Session Description Protocol (SDP) format. This description includes the streaming communication parameters, such as the types of media to be exchanged, codecs and their settings, and bandwidth information. Upon receiving the offer, the Server creates an answer for connecting to the endpoint. After having checked the information in response is correct, the peers establish a connection, and the Plugin can finally send the media stream to the client, passing through the server. The first part of the communication, i.e., between the Plugin and the server, occurs via ffmpeg, while the second part, i.e., between the client and the server, is managed by the transmission manager.

Example 7: Image Processing

Typical image processing operations performed on the samples may include color deconvolution, nuclear and mitotic counts on tumor cells, tumor pattern detection as the user moves the image, etc. Machine learning algorithms are under rapid development to assist with the latter. The image processing application may be written in Java and use standard libraries such as ImageJ and OpenCV.

Currently, in several occasions pathologists manually count expressed cells. The count of cells that co-express (Olig-2 and Ki-67 histological markers) is used to assess tumor proliferation by immunohistochemical methods, particularly in neuroendocrine tumors and hence can change the course of an active surgery or a treatment. Currently, quantification is done predominately by hand-counting positive and negative nuclei on selected regions of the tissue. While software packages that distinguish immunohistochemically positive and negative cells exist, they do so on merely single photographs of selected regions. The present system allows the entire virtual slide to be processed (more than a single photograph) using high computational power present within a regional network, i.e., at the edge, or remotely, using virtual network paths with reserved bandwidth.

Figure 5A:
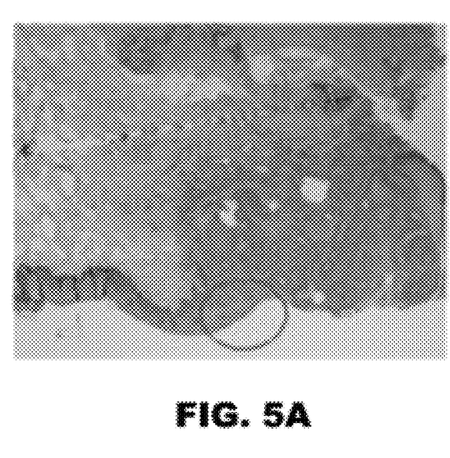
FIG. 5A is a view of invasive squamous cell carcinoma of a tongue, with tumor area highlighted in the red circle at 2× magnification.
Figure 5B:
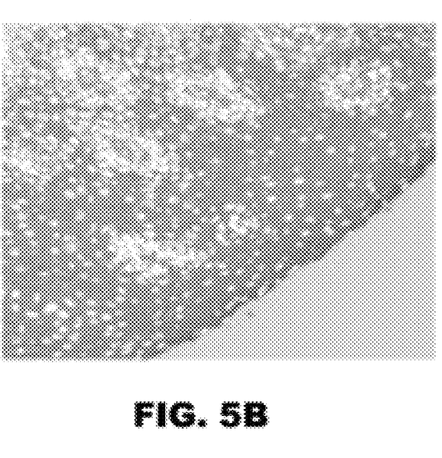
FIG. 5B is an image after the application of nuclei detection algorithm at 10× magnification; in addition to the image, information about percentage of marker co-expression in the sample is automatically provided to the web interface.

FIGS. 5A-5B show an example of image processing aiming to count the affected nuclei. The counting is recomputed every time the image is moved or zoomed. The knowledge of the percentage of cells activated by different markers (represented by different colors), can be used by the pathologist to assess the tumor grade, a parameter for the course of an active surgery, or a treatment.

Figure 6A:
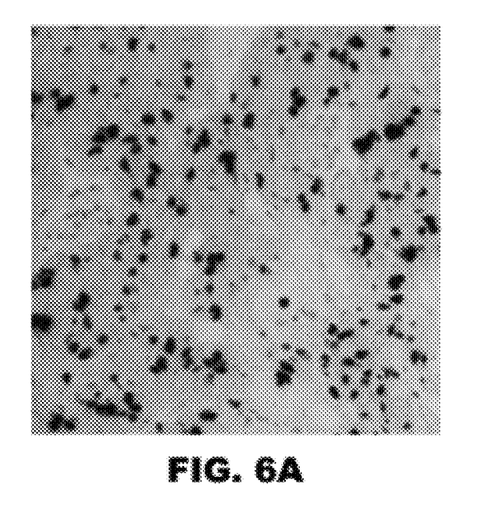
FIG. 6A shows a sample with highlighted proliferative endothelial cells in blood vessels plus rare positive tumor cells.
Figure 6B:
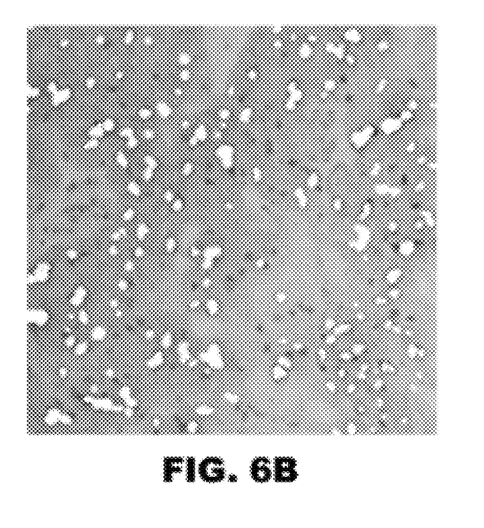
FIG. 6B is an image after the application of tumor detection algorithm; in addition to the image, information about percentage of tumor in the sample is provided to pathologist.

FIGS. 6A-6B show how the algorithm detects inked Olig2, particularly used for neural stem cell and progenitor cell proliferation. This information can be exploited to subtract areas negative for GFAP and Olig2 during a Ki67 count, assuming stains are performed on the same slide in different colors.

Figure 7A:
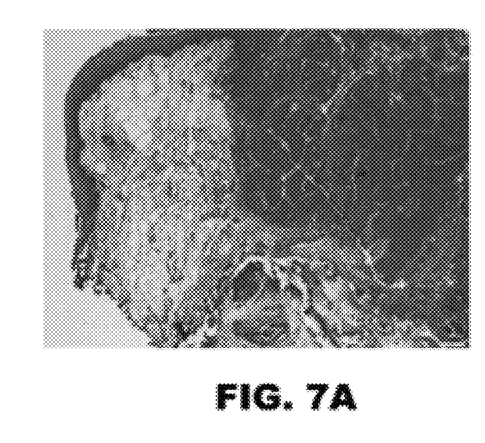
FIG. 7A is an example tumor before application of an algorithm for margin detection.
Figure 7B:
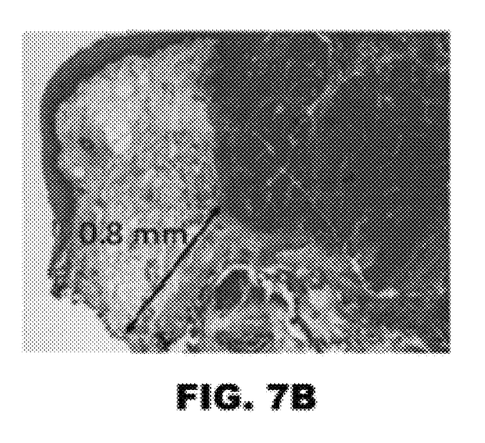
FIG. 7B is an example of distance tumor to margin operation by means of an algorithm that automatically detects the margin.

In FIGS. 7A-7B, the distance from the tumor and the margin was measured, inked at the left side. The pathologist marks the tumor, and the algorithm automatically detects the margin and computes the distance between the two points. The tumor may be automatically detected as well, when the pathologist selects the area of interest. Distance is returned in "mm". As demonstrated by previous solutions, this information is extremely significant, but sometimes it is computed by hand by pathologists. The distance from tumor-to-margin is typically reported in oral cavity malignancies (usually, squamous cell carcinoma), as it has been shown to impact prognosis when the margin is less than 5 mm. Before the gross specimen is sectioned and sampled in cassettes for histology, inking is performed, making it easy to detect it for a computer-based algorithm. Automatic calculation of the closest distance between the tumor and specimen margin (edge) can greatly decrease evaluation time and reporting accuracy. The distance can also be used in breast cancer specimens, with particular interest on the distance from an invasive and in-situ tumor in the standardized reporting forms.

The edge computing paradigm allows performing of fast and intensive processing otherwise impossible to obtain on a local machine. With the aim of reducing response time, and so the diagnosis turnaround time, it is first checked whether the requested image is already in memory. If so, the software retrieves it, and the processing algorithm (if configured by the user) is applied. The user can also specify if a compression needs to be applied over the final image. In this case, the image is sent after a lossless compression. In case of urgent analysis, a lossy compression algorithm can be requested and applied, where the compression quality is a customizable parameter. The compression quality is a value between 0 and 1: a compression quality setting of 0:0 means that the highest compression must be applied, while a setting of 1:0 can use images of high quality. In a lossy compression schema, the compression quality determines the trade-off between file size and image quality, by choosing quantization tables when writing JPEG images. For lossless instead, the compression quality is used to control the trade-off between file size and time taken to perform the compression, by optimizing row filters and setting the compression level when writing the final image.

If the image is not in memory, it is retrieved from the database, and then the same procedure described above was followed. In this case, however, the image is locally saved in order to avoid the transfer delay in case the pathologist will come back to work on the same sample.

The presented procedure works for offline images, while for images snapped during the live session, a lossy compression algorithm is applied (unless otherwise specified) as they have to be retrieved from the microscope.

In the following, counting nuclei and tumor-to-margin distance are two examples of image processing which can be applied either in real-time for captures of the microscope, or offline for stored samples. Before the application of such algorithms, it is often required to regularize the image, typically via a stain normalization, in order to increase the accuracy of following image operations.

The procedure of staining the tissue sections affects the appearance of H&E histology samples, and it can vary significantly across laboratories, but even across samples within the same lab. Although this variability partially limits the interpretation of images by pathologists, it may affect the result of subsequent image analysis algorithms. To address this problem, Stain Normalization (SN) algorithms are able to match stain colors of histological images with a given template. Formally, SN consists in transforming an image I into another image I* via a function f, I*=f(θ; I), where θ denotes a set of parameters extracted from a template image t. θ includes the parameters that are generally defined to capture color information of the main stain components in the image, such as H and E. The final result I* is a stain-normalized image whose distribution of colors resembles the ones of the template t. An algorithm may be applied if specified by the user.

Figure 8:
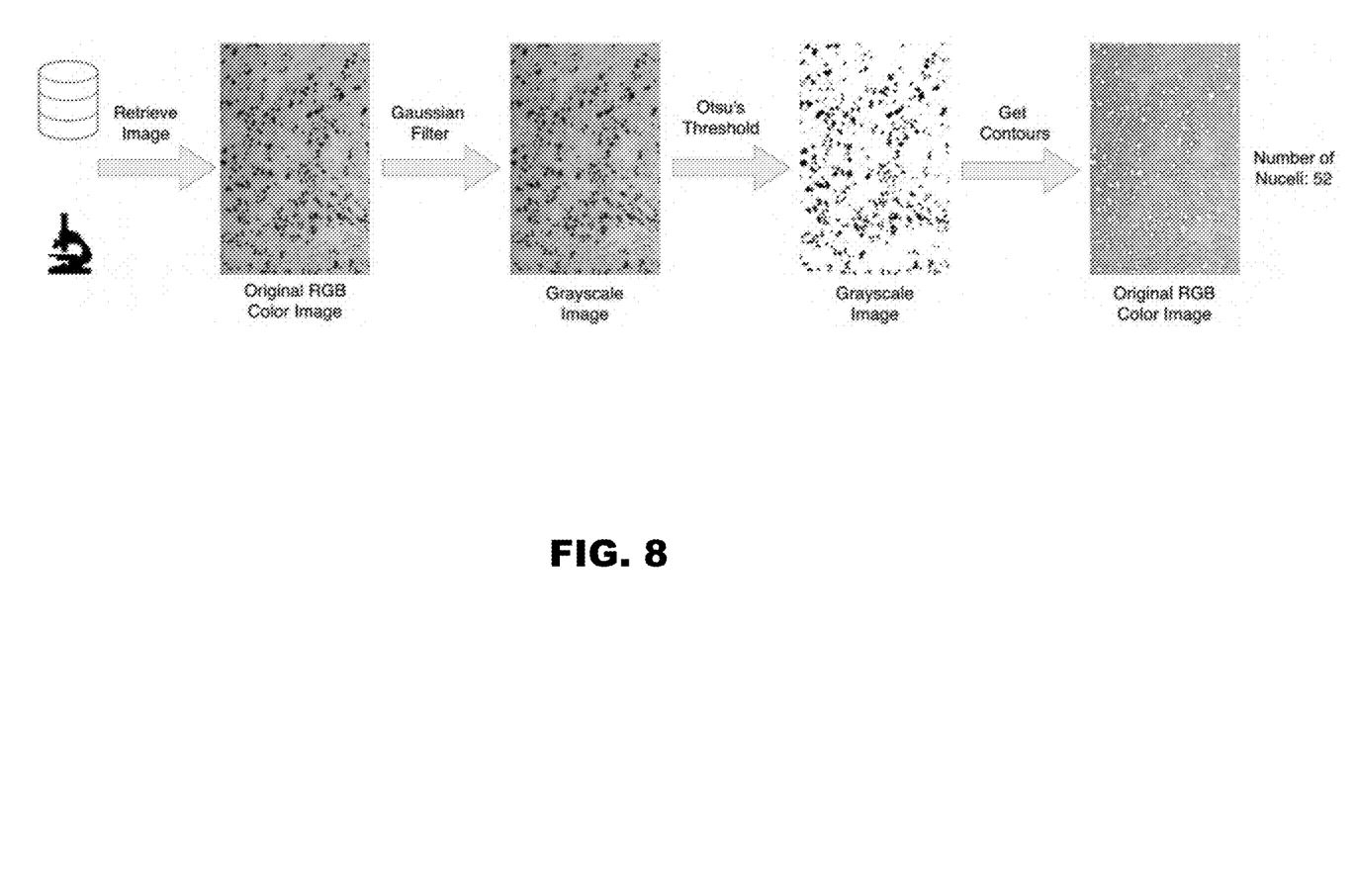
FIG. 8 is an example count nuclei computation and image processing pipeline to extract cells information, such as the overall number and the position inside the image.

In FIG. 8, an example methodology is used for the count nuclei task. First, the image is retrieved either in real-time from the microscope or offline from the database/memory, and the user labels the Region of Interest (ROI). The ROI boundaries are set using the interface, which provides commands to select an area on the image. However, if not specified, the program assumes the ROI as the whole image and continues the pipeline in the same way. One of the advantages of edge processing is indeed the possibility to perform computations on the whole slide image, which would be extremely power- and time-consuming on local machines. After converting the image to grayscale, a Gaussian filter is applied to blur the image and to reduce noise. The Gaussian filter is a linear filter, usually adopted for low-pass frequency filters, since its effect is to remove high spatial frequency components from an image, thus reducing the contrast of the sample. In the Examples, the value of sigma in the Gaussian filter was 0 and a kernel size of 5×5 pixels was used.

As the third step, segmentation was applied through the Otsu's method to perform automatic image thresholding. This algorithm finds the threshold that minimizes the weighted within-class variance and returns the image whose pixels are either black or white. On the obtained image, the detection of contours is indeed easier, due to the high contrast between black and white pixels. Thus, the contours are easily extracted using the algorithm, and are drawn on the final image so that pathologists can observe them even in the RGB colored image. As additional information, the number of found contours n are provided, which is used by the pathologist.

If necessary, the pathologist can decide to show the nuclei centroids for the sake of improved visibility and clarity of the image. In this case, nuclei centroids were detected as the moments of centroids of connected targets in a binary image, through the Green's formula.

A second algorithm formalizes the operations performed to obtain the distance from tumor-to-margin with an uncertainty of g. Once the ROI, defined by the main malignant area within the pathology image, is set, the pathologist marks the tumor as a point m in the image. Considering that the margin of the cell is usually inked, e.g., as in FIGS. 7A-7B, a computer algorithm can rapidly detect the margin contours using a procedure to identify pixels of a specific color. Then, the maximal distance initializes v, which is computed as the minimum length between m and the edges of the ROI. This value is quickly obtained through four comparisons of location m, with the four borders, and is then multiplied by the ratio to get the distance in "mm". The minimal distance p is instead initialized to 0.

After this first initialization phase, an iterative search starts, aiming to find the distance as the radius of a circumference centered in m. The first part is a binary search of a circumference that intersects the cell's margin. Binary search is a well-known approach to find the position of a target value within an array. In this case, the algorithm has the contour CO as target and compares this target to the circumference circ with a radius equal to the middle of all possible distances, i.e., a number between p and v. If circ and CO are not crossed, the half in which the target cannot lie is eliminated, and the search continues on the remaining half, again taking the radius r as the middle element to compare, and repeating this until the target value is found. By leveraging binary search, the number of iterations may be reduced, compared to other iterative search techniques that are more time-consuming.

When the circumference is found, ext is set to true, and the second part starts. Given the valid circumference identified at the end of the first section, the value of r is minimized to reach the minimal distance between the target and m. In fact, the circ found is clearly valid, but it might not be the smallest circumference that meets the target shape. For this reason, r is iteratively decreased until the derived circ resides outside the target. At this point, the distance is the last value of r plus the granularity g. Finally, the algorithm returns the distance with an uncertainty g, and this value is reported in the image, in a way that pathologists can use this information for subsequent operations.

The granularity value g significantly affects the number of iterations and, consequently, the overall time. However, despite the default value of 0:1 mm that was set since it is reasonable in most of the cases, it can be customized by the pathologist to tailor the specific use case.

Example 8: Evaluation Scenario and Testbed

To establish the practicality of the telepathology system design, a testbed was developed to be deployed on system servers and on CloudLab. To test the edge computing-based telepathology system, the emulated version of the microscope as described in Examples 1-7 was used. Second, the algorithms implemented were evaluated in terms of accuracy and computation time. Third, system performance and resource usage were measured in order to assess the practicality of the approach. Finally, experiments were conducted over a real microscope to quantify the overhead due to physical device effects. All services were installed across three physical machines while the VMs were deployed by the OpenStack orchestrator.

To evaluate the telepathology system, and in particular the computer-aided image processing, microscopic samples were retrieved from an online database.

Example 9: Cloud, Edge, and Image Processing Orchestration for Remote Computation In-cloud deep-learned analysis of histological images may be tested. The diagnosis (structured text data) may be considered a "label" to be used for training a supervised machine-learning system for image classification. It may be assessed what visualization is used to present this projection to the pathologist at the edge; what deployment mechanism is selected once the deep-learned system is available; and/or if process running the system be executed in the cloud or moved to the edge.

Example 10: Remote Pathology Consultation

Allowing remote control of such pathology actions on a microscope, i.e. on software-defined glass slides, is fundamentally different than a video conference. In a telepathology system, the resolution, responsiveness and size of the histological images to transfer and pre-process are much higher/larger. Both low delays and high bandwidth are on a dedicated virtual path that does not compete with other Internet traffic or internal campus network data flows.

Figure 11:
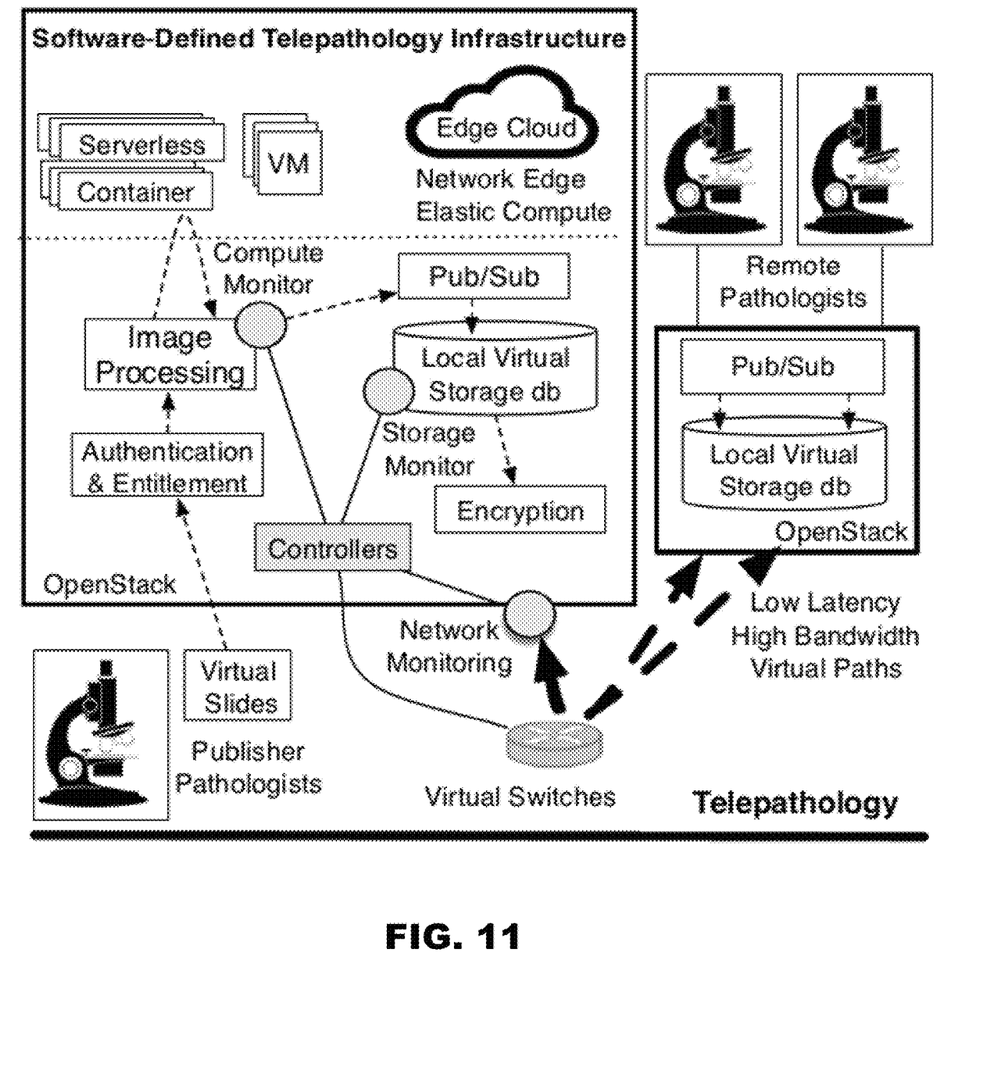
FIG. 11 shows an architecture overview of a software-defined telepathology infrastructure (SDTI).

Example 11: A Software-Defined Telepathology Infrastructure (SDTI): Design and Implementation FIG. 11 illustrates an implementation of the Software-Defined Telepathology Infrastructure or SDTI. The system focus is on the adaptability of virtual nodes and virtual paths hosting histological digital images. In particular, a virtual slide management architecture and an object model will be designed and implemented in support of a responsive, telepathology architecture. The system will be deployed using local resources as well as CPUs/GPUs and regular cloud resources.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure, to the full extent indicated by the broad general meaning of the terms used in the attached claims. It will therefore be appreciated that the examples described above may be modified within the scope of the appended claims.

What is claimed is:

1. A telepathology system associated with an edge network shared among participating users, comprising:
    a microscope comprising a camera operable to receive image data of a specimen on a microscope platform;
    one or more processors connected to the edge network; and
    a memory storing instructions that, when executed by the one or more processors, causes the one or more processors to:
        receive image data from the camera;
        pre-process the image data at network edge;
        send the pre-processed image data digitally to the participating users;
        receive control instructions from the user, wherein the control instructions, when executed by the one or more processors, cause the one or more processors to control the image data;
        assign a dedicated virtual node instance selected from a Virtual Machine (VM) or a Lightweight Virtual Machine to each participating user; and
        process the image data to identify a property of the specimen, wherein the property of the specimen is selected from color decomposition, cell count, count of nuclei of proliferating tumor cells, detection of a pattern tumor with a static image, detection of a pattern tumor as the participating user moves the image, percentage of cells activated by different markers, or combinations thereof.

2. The telepathology system of claim 1, wherein the memory stores further instructions to:
    speed up image transmission time or perform application-specific image processing.

3. The telepathology system of claim 1, wherein the control of the image data is selected from moving the microscope platform, panning, zooming, or capturing at least one additional image for live or subsequent processing.

4. The telepathology system of claim 1, wherein the image data is a still image or a video.

5. The telepathology system of claim 4, wherein the image data is video and the memory stores further instructions to live stream the specimen to the participating users.

6. The telepathology system of claim 5, wherein the edge network pre-processes the stream, compressing its payload.

7. A telepathology method comprising:
    receiving, via one or more processors connected to an edge network, image data from a microscope comprising a camera operable to receive image data of a specimen on a microscope platform, wherein the microscope is associated with the edge network shared among participating users;
    pre-processing the image data at network edge;
    sending the pre-processed image digitally to the participating users;
    controlling the image data, via instructions from the participating users;
    assigning a dedicated virtual node instance selected from a Virtual Machine (VM) or a Lightweight VM to each participating user; and
    processing the image data to identify a property of the specimen, wherein the property of the specimen is selected from color decomposition, cell count, count of nuclei of proliferating tumor cells, detection of a pattern tumor with a static image, detection of a pattern tumor as the participating user moves the image, percentage of cells activated by different markers, or combinations thereof.

8. The telepathology method of claim 7, further comprising:
    speeding up image transmission time or performing application-specific image processing.

9. The telepathology method of claim 7, wherein controlling of the image data is selected from moving the microscope platform, panning, zooming, or capturing at least one additional image for live or subsequent processing.

10. The telepathology method of claim 7, wherein the image data is a still image or a video.

11. The telepathology method of claim 10, wherein the image data is video and sending the image data comprises live streaming the specimen to the participating users.

12. The telepathology method of claim 11, wherein the edge network pre-processes the stream, compressing its payload.

* * * * *